United States Patent
Ha et al.

(10) Patent No.: US 9,918,875 B2
(45) Date of Patent: Mar. 20, 2018

(54) CONTACT LENS ASSEMBLY AND OPHTHALMIC TREATMENT APPARATUS COMPRISING SAME

(71) Applicant: LUTRONIC CORPORATION, Goyang (KR)

(72) Inventors: Tae Ho Ha, Goyang (KR); Jong Woong Lee, Seoul (KR)

(73) Assignee: LUTRONIC CORPORATION, Goyang (KR)

( * ) Notice: Subject to any disclaimer, the term of this patent is extended or adjusted under 35 U.S.C. 154(b) by 71 days.

(21) Appl. No.: 14/414,695

(22) PCT Filed: Jul. 15, 2013

(86) PCT No.: PCT/KR2013/006325
§ 371 (c)(1),
(2) Date: Jan. 13, 2015

(87) PCT Pub. No.: WO2014/011013
PCT Pub. Date: Jan. 16, 2014

(65) Prior Publication Data
US 2015/0164686 A1    Jun. 18, 2015

(30) Foreign Application Priority Data
Jul. 13, 2012  (KR) .................. 10-2012-0076778

(51) Int. Cl.
*A61F 9/00*    (2006.01)
*A61F 9/008*   (2006.01)
*A61F 9/009*   (2006.01)

(52) U.S. Cl.
CPC .............. *A61F 9/009* (2013.01); *A61F 9/008* (2013.01); *A61F 9/00821* (2013.01); *A61F 2009/00868* (2013.01); *A61F 2009/00891* (2013.01)

(58) Field of Classification Search
CPC .. A61F 2009/00868; A61F 2009/00891; A61F 9/008; A61F 9/00821; A61F 9/009
USPC .......................................... 606/4–6
See application file for complete search history.

(56) References Cited

U.S. PATENT DOCUMENTS

| | | | |
|---|---|---|---|
| 3,820,879 A * | 6/1974 | Frisen | A61B 3/125 351/200 |
| 7,441,899 B2 | 10/2008 | Eisenberg et al. | |
| 7,692,865 B2 * | 4/2010 | Muhlhoff | A61F 9/00827 359/634 |

(Continued)

FOREIGN PATENT DOCUMENTS

JP    2007-510478 A    4/2007

OTHER PUBLICATIONS

International Search Report for PCT/KR2013/006325, dated Oct. 25, 2013.

*Primary Examiner* — Lynsey Eiseman
*Assistant Examiner* — Jonathan Kuo

(57) ABSTRACT

The present invention relates to a contact lens assembly and to an ophthalmic treatment apparatus comprising same. The contact lens assembly according to the present invention comprises: a housing arranged on the cornea of an eyeball so as to guide the treatment beam radiated onto the eyeball; and a reflection unit arranged inside the housing so as to radiate the treatment beam guided to the inside of the housing to a plurality of irradiation points along the outer circumferential direction of the eyeball around the pupil of the eyeball.

9 Claims, 7 Drawing Sheets

(56) References Cited

U.S. PATENT DOCUMENTS

2005/0174538 A1     8/2005  Eisenberg
2005/0288745 A1*   12/2005  Andersen ............ A61F 9/00781
                                                      607/86
2012/0050683 A1*    3/2012  Yates ................... A61B 3/1208
                                                      351/219

* cited by examiner

CONTACT LENS ASSEMBLY AND OPHTHALMIC TREATMENT APPARATUS COMPRISING SAME

BACKGROUND OF THE INVENTION

Field of the Invention

The present invention relates to a contact lens assembly and an ophthalmic treatment apparatus including the same and, more particularly, to a contact lens assembly for treating glaucoma and an ophthalmic treatment apparatus including the same.

Related Art

In general, the diseases of an eyeball are basically divided into glaucoma, a cataract, macular degeneration, etc. Glaucoma is a disease of an eyeball in which lacrimal gland, etc. are occluded and thus intraocular pressure within the eyeball is increased, a cataract is a disease of an eyeball in which the crystalline lens is whitened, and macular degeneration is a disease of an eyeball that is generated in the retina.

A method of treating glaucoma of such diseases of an eyeball includes radiating a beam for treatment, such as a laser, to the ciliary body of the outer circumference of the cornea in order to reduce intraocular pressure of an eyeball, that is, vitreous humour.

Meanwhile, a conventional glaucoma treatment apparatus has been disclosed in "Korean Patent Application Publication No. 2003-0092736" entitled "Glaucoma Treatment Apparatus Using a Semiconductor Laser." The "glaucoma treatment apparatus using a semiconductor laser", that is, the aforementioned prior art, includes treatment means for radiating a guide beam in response to an operator's manipulation so that a treatment location is checked and a laser beam of an IR region is radiated to the tissue of the treatment location in order to treat glaucoma through photocoagulation and output means for enabling the operator to be aware of the current operating status of the treatment means.

However, the "glaucoma treatment apparatus using a semiconductor laser" disclosed in the conventional prior document is problematic in that the time taken for treatment is increased because the glaucoma treatment apparatus must be moved to each radiation location so that a laser beam is radiated along the outer circumference of the cornea at a specific interval.

SUMMARY OF THE INVENTION

An object of the present invention is to provide a contact lens assembly having an improved method of radiating a beam for treatment so that a beam for treatment radiated for glaucoma treatment is radiated along the circumference of the cornea at specific intervals and an ophthalmic treatment apparatus including the same.

According to the present invention, means for solving the object is accomplished by a contact lens assembly for treating glaucoma, including a housing which is disposed on the cornea of an eyeball and guides a beam for treatment radiated to the eyeball and a reflection unit which is disposed within the housing and guides the beam for treatment guided to the inside of the housing to a plurality of radiation locations in the outer circumferential direction of the eyeball around a pupil of the eyeball.

In this case, the reflection unit preferably has a rotational axial line in a direction perpendicular to a direction in which the beam for treatment is incident and is subject to a rotational motion so that the beam for treatment is radiated to the plurality of radiation locations in the outer circumferential direction of the eyeball at specific intervals.

The reflection unit may include a mirror unit which is disposed within the housing and reflects the beam for treatment incident on the inside of the housing and a driving unit which is connected to the mirror unit and provides a driving force so that the mirror unit is subject to the rotational motion.

Preferably, a plurality of the reflection units may be disposed at specific intervals within the housing depending on a turn angle of the reflection unit.

Furthermore, preferably, the reflection unit may be provided in a sheet form, and a plurality of the reflection units may be disposed along an inner circumferential surface of the housing so that a location where the beam for treatment is radiated is moved in the outer circumferential direction of the eyeball.

Furthermore, preferably, the reflection unit may have curvature corresponding to curvature of the inner circumference of the housing and may be provided to have a specific length along the inner circumferential surface of the housing so that a location where the beam for treatment is radiated is moved in the outer circumferential direction of the eyeball.

In contrast, the reflection unit may include a mirror unit of a sheet form which is disposed within the housing and reflects the beam for treatment incident on the inside of the housing in the outer circumferential direction of the eyeball and a driving unit which moves the mirror unit along an inner circumferential surface of the housing so that the mirror unit reflects the beam for treatment in the outer circumferential direction of the eyeball.

Meanwhile, according to the present invention, means for solving the object is accomplished by an ophthalmic treatment apparatus for treating glaucoma, including a beam generation unit which generates a beam for treatment, a beam delivery unit which guides the beam for treatment generated by the beam generation unit to an eyeball, and the aforementioned contact lens assembly disposed between the eyeball and the beam delivery unit.

In this case, preferably, the beam delivery unit may control the radiation path of the beam for treatment that is incident from the beam generation unit and that is radiated to the contact lens assembly.

The details of other embodiments are included in the detailed description and the drawings.

The contact lens assembly and the ophthalmic treatment apparatus including the same according to the present invention is advantageous in that a beam for treatment can be radiated to a plurality of radiation locations in a short time because the reflection unit for illuminating a plurality of radiation locations is disposed in the outer circumferential direction of an eyeball and thus treatment efficiency can be improved.

DESCRIPTION OF EXEMPLARY EMBODIMENTS

Figure 1:
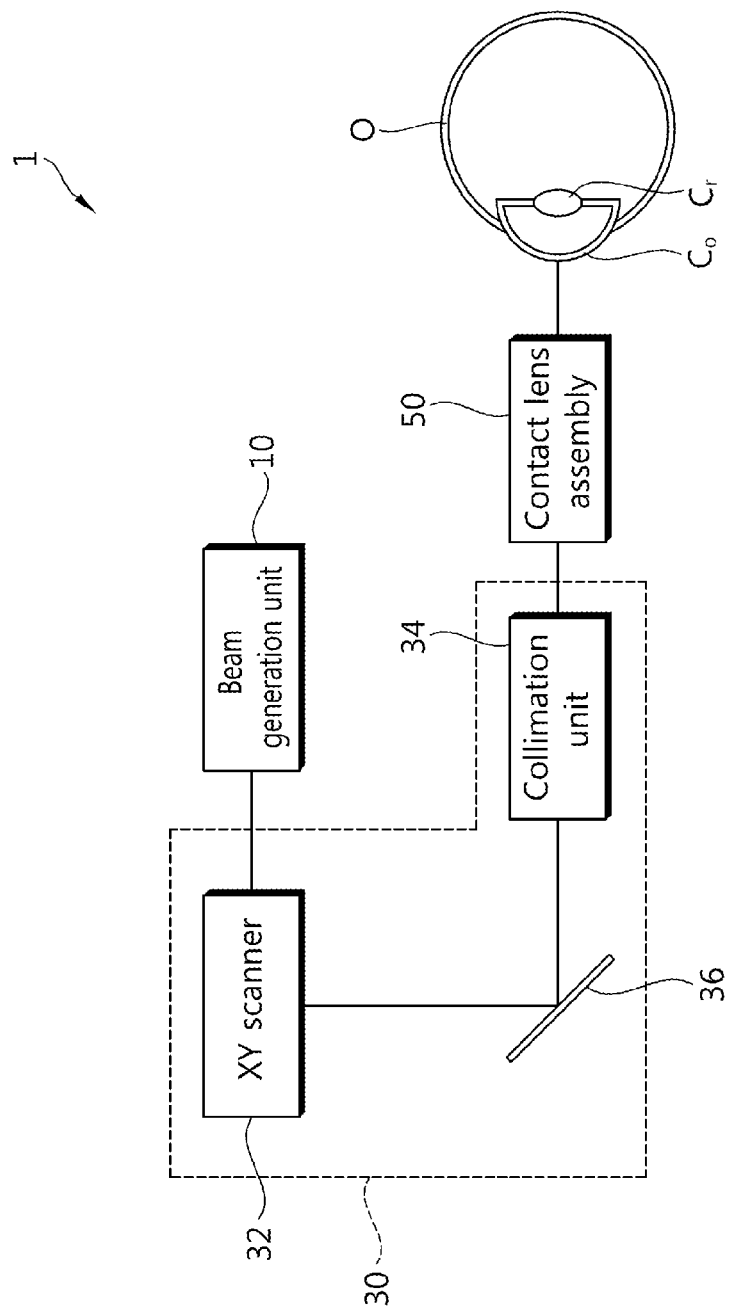
FIG. 1 is a schematic configuration diagram of an ophthalmic treatment apparatus in accordance with a first embodiment of the present invention.

Hereinafter, contact lens assemblies and ophthalmic treatment apparatuses including the same in accordance with embodiments of the present invention are described in detail with reference to the accompanying drawings.

Prior to a description, it is to be noted that although a beam generation unit and a beam delivery unit, that is, elements of ophthalmic treatment apparatuses in accordance with first to fourth embodiments of the present invention, are assigned the same reference numerals, the contact lens assemblies and their subordinate elements, that is, characteristics of the embodiments, are assigned different numerals even if they have the same names.

<First Embodiment>

Figure 2:
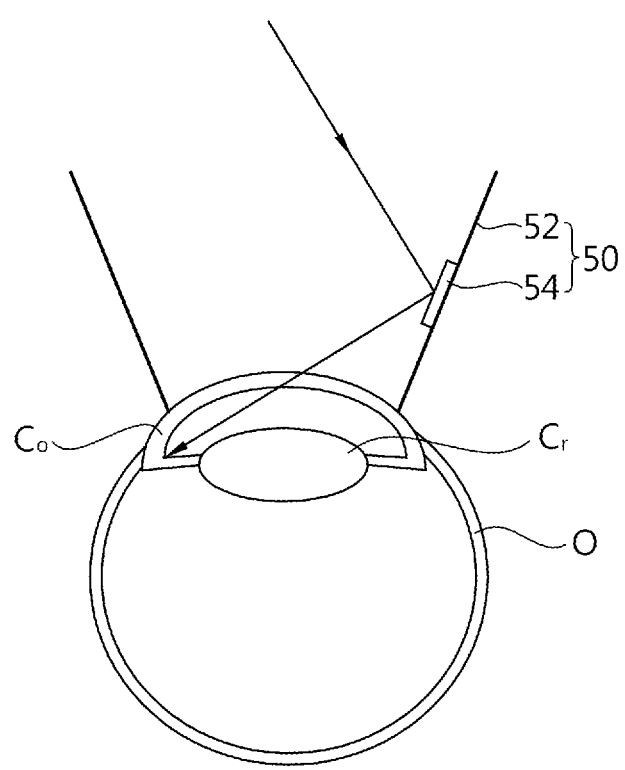
FIG. 2 is a diagram illustrating the operation of the contact lens assembly of the ophthalmic treatment apparatus in accordance with the first embodiment of the present invention.
Figure 3:
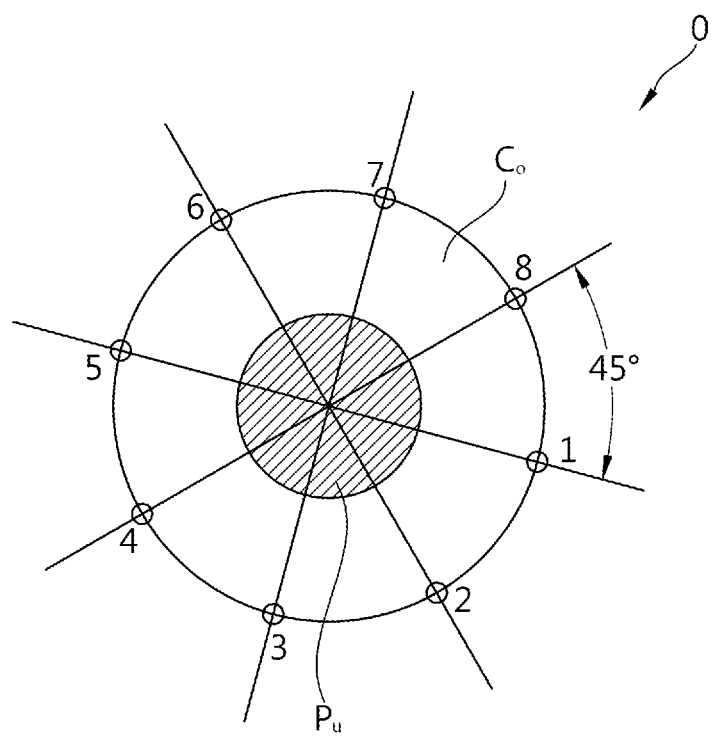
FIG. 3 is a diagram illustrating locations where beams for treatment are radiated using the contact lens assembly of the ophthalmic treatment apparatus in accordance with the first embodiment of the present invention, FIG. 4 a plan view illustrating the operation of the contact lens assembly of the ophthalmic treatment apparatus in accordance with the first embodiment of the present invention.
Figure 4:
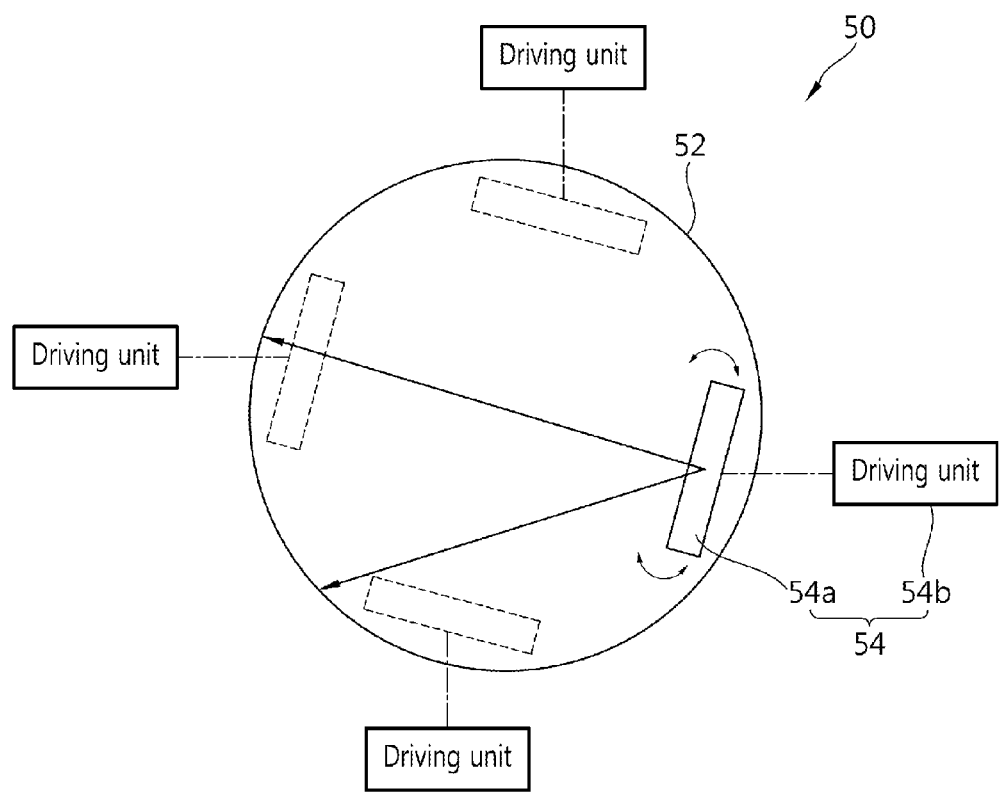

FIG. 1 is a schematic configuration diagram of an ophthalmic treatment apparatus in accordance with a first embodiment of the present invention, FIG. 2 is a diagram illustrating the operation of the contact lens assembly of the ophthalmic treatment apparatus in accordance with the first embodiment of the present invention, FIG. 3 is a diagram illustrating locations where beams for treatment are radiated using the contact lens assembly of the ophthalmic treatment apparatus in accordance with the first embodiment of the present invention, and FIG. 4 a plan view illustrating the operation of the contact lens assembly of the ophthalmic treatment apparatus in accordance with the first embodiment of the present invention.

As illustrated in FIGS. 1 to 4, the ophthalmic treatment apparatus 1 in accordance with the first embodiment of the present invention includes a beam generation unit 10, a beam delivery unit 30, and a contact lens assembly 50. The ophthalmic treatment apparatus 1 in accordance with an embodiment of the present invention guides a beam for treatment, generated by the beam generation unit 10, to the beam delivery unit 30 and the contact lens assembly 50 and radiates the beam for treatment to the ciliary body of an outside circumference of the cornea Co of an eyeball O, that is, a ciliary body supporting the crystalline lens Cr, in order to treat glaucoma.

The beam generation unit 10 is provided in order to generate a beam for treatment. The beam generation unit 10 generates a laser as a beam for treatment. The laser generated by the beam generation unit 10 has a wavelength band that may be applied to the ciliary body of the outside circumference of the cornea Co. In this case, the beam generation unit 10 may include a resonator or laser diode including a laser medium so that the laser is generated as the beam for treatment.

The beam delivery unit 30 guides a beam for treatment, generated by the beam generation unit 10, to the contact lens assembly 50. The beam delivery unit 30 includes an XY scanner 32, a collimation unit 34, and a beam splitter 36.

The XY scanner 32 is provided in order to control a location where a beam for treatment is radiated on an XY plane, that is, a direction perpendicular to the optical axial line of the beam for treatment. The XY scanner 32 includes at least two mirrors (not illustrated) for controlling a location where a beam for treatment is radiated on the XY plane.

In this case, the beam generation unit 10 or the beam delivery unit 30 may further include a shutter (not illustrated) for selectively radiating a beam for treatment to an affected part. The shutter can prevent a beam for treatment from being consecutively radiated while a radiation location is changed by the beam delivery unit. Furthermore, control may be performed so that a beam for treatment is radiated after a change into a desired radiation location and a beam for treatment is radiated after the radiation location is changed again.

The collimation unit 34 guides a beam for treatment incident from the XY scanner 32 to the contact lens assembly 50. The collimation unit 34 is formed of an object lens. The beam splitter 36 is disposed between the XY scanner 32 and the collimation unit 34 and guides a beam for treatment from the XY scanner 32 to the collimation unit 34.

The contact lens assembly 50 includes a housing 52 and reflection units 54. The contact lens assembly 50 reflects an incident beam for treatment to radiation locations so that the beam for treatment is radiated to the ciliary body of the outside circumference of the cornea Co at specific intervals.

The housing 52 is disposed on the cornea Co of the eyeball O, and it guides a beam for treatment that is radiated to the eyeball O. That is, the housing 52 comes in contact with the cornea Co of the eyeball O. The housing 52 has a conical shape of a trapezoid, that is, cross-sectional shape having both sides open.

The reflection units 54 are disposed within the housing 52, and they radiate beams for treatment guided to the inside of the housing 52 to a plurality of radiation locations in the outer circumferential direction of the eyeball O around the pupil Pu of the eye of the eyeball O. The reflection unit 54 performs a rotational motion with a rotational axial line in a direction perpendicular to the direction in which a beam for treatment is incident so that the beam for treatment is radiated to a plurality of radiation locations at specific intervals in the outer circumferential direction of the eyeball O. The reflection units 54 are disposed at specific intervals within the housing 52 depending on a turn angle.

That is, as illustrated in FIG. 3, a plurality of the reflection units 54 is disposed so that beams for treatment are radiated to radiation locations '1 to 8.' For example, as illustrated in FIG. 4, four reflection units 54 may be provided so that beams for treatment are radiated to respective radiation locations '1 and 2', '3 and 4', '5 and 6', and '7 and 8.' However, the reflection units 54 illustrated in FIGS. 3 and 4 are only an embodiment, and the number of reflection units 54 may be changed depending on the number of radiation locations. The reflection unit 54 according to the first embodiment of the present invention includes a mirror unit 54a and a driving unit 54b.

The mirror unit 54a is provided in order to reflect a beam for treatment guided to the inside of the housing 52 toward a radiation location. Four mirror units 54a are disposed at equal intervals in the circumferential direction in such a way as to correspond to the four reflection units 54. The mirror unit 54a may be configured to rotate at a specific angle on a plane that forms the circular cross section of the contact lens assembly. (Alternatively, the mirror unit 54a performs a rotational motion with a rotational axial line in a direction perpendicular to the direction in which a beam for treatment is incident.

The driving unit 54b is connected to the mirror unit 54a, and it performs a rotational motion on the mirror unit 54a. The driving unit 54b is provided so that it corresponds to the number of mirror units 54a. The driving unit 54b generates a driving force so that the mirror unit 54a is subject to a rotational motion and provides the driving force to the mirror unit 54a.

<Second Embodiment>

Figure 5:
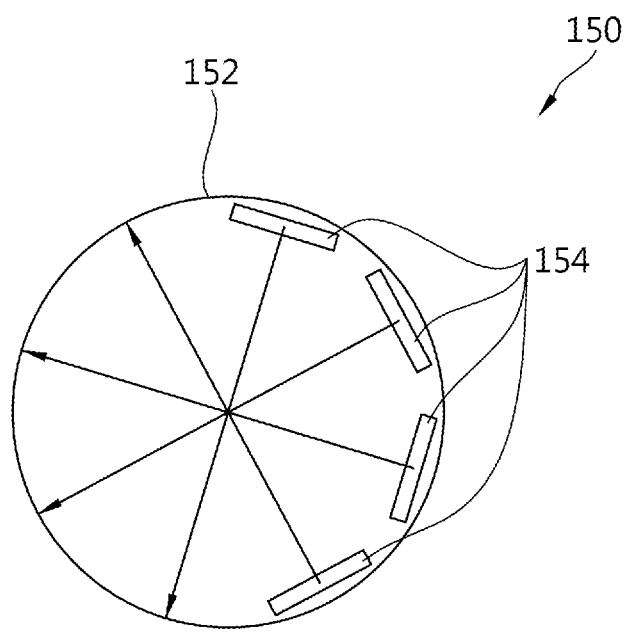
FIG. 5 is a plan view illustrating the operation of the contact lens assembly of an ophthalmic treatment apparatus in accordance with a second embodiment of the present invention.

FIG. 5 is a plan view illustrating the operation of the contact lens assembly of an ophthalmic treatment apparatus in accordance with a second embodiment of the present invention.

As illustrated in FIG. 5, the ophthalmic treatment apparatus 1 in accordance with the second embodiment of the present invention includes the beam generation unit 10, the beam delivery unit 30, and a contact lens assembly 150. In this case, the beam generation unit 10 and the beam delivery unit 30 are the same as those of the first embodiment, and detailed descriptions thereof are omitted.

The contact lens assembly 150 in accordance with the second embodiment of the present invention includes a housing 152 and reflection units 154. Each of the reflection units 154 is provided in a sheet form. A plurality of the reflection units 154 is disposed on the inner circumferential surface of the housing 152 so that a location where a beam for treatment is radiated is moved in the outer circumferential direction of the eyeball O. Beams for treatment can be radiated to a plurality of radiation locations because the plurality of reflection units 154 is disposed at equal intervals on the inner circumferential surface of the housing 152 as described above.

<Third Embodiment>

Figure 6:
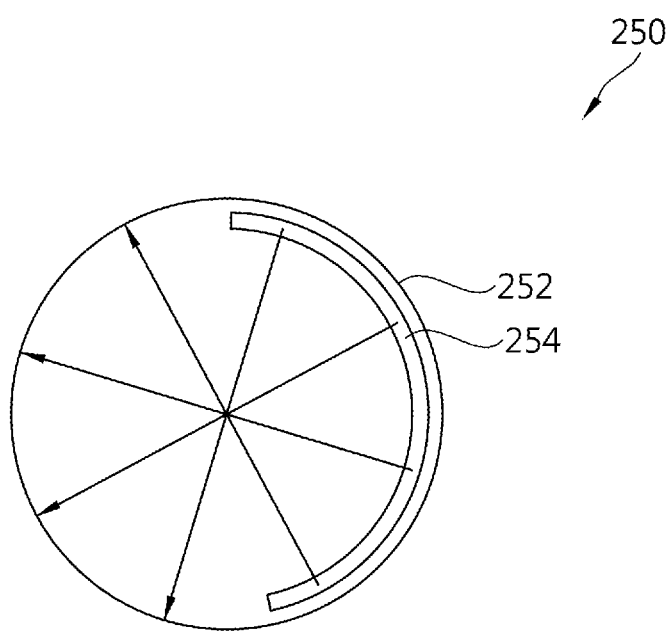
FIG. 6 is a plan view illustrating the operation of the contact lens assembly of an ophthalmic treatment apparatus in accordance with a third embodiment of the present invention.

FIG. 6 is a plan view illustrating the operation of the contact lens assembly of an ophthalmic treatment apparatus in accordance with a third embodiment of the present invention.

The ophthalmic treatment apparatus 1 in accordance with the third embodiment of the present invention includes the beam generation unit 10, the beam delivery unit 30, and a contact lens assembly 250, as illustrated in FIG. 6.

The contact lens assembly 250, that is, a technical characteristic of the ophthalmic treatment apparatus 1 in accordance with the third embodiment of the present invention, includes a housing 252 and a reflection unit 254. The reflection unit 254 has curvature corresponding to the curvature of the inner circumference of the housing 252, and it is disposed on the inner circumferential surface of the housing 252. The reflection unit 254 having curvature has a specific length along the inner circumferential surface of the housing 252 so that a location where a beam for treatment is radiated is moved in the outer circumferential direction of the eyeball O. The reflection unit 254 reflects a beam for treatment that is incident on the inside of the housing 252 and radiates the beam to a plurality of radiation locations because the reflection unit 254 having curvature corresponding to the curvature of the inner circumference of the housing 252 is disposed in a specific length as described above.

<Fourth Embodiment>

Figure 7:
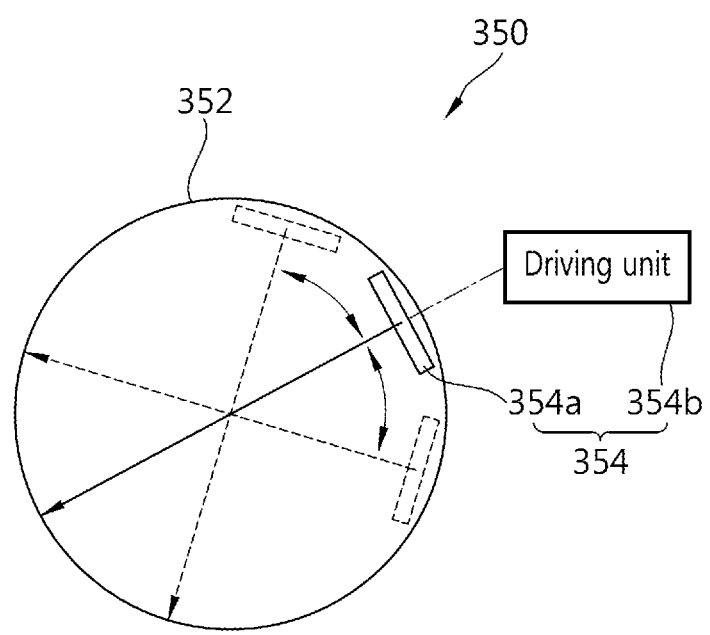
FIG. 7 is a plan view illustrating the operation of the contact lens assembly of an ophthalmic treatment apparatus in accordance with a fourth embodiment of the present invention.

FIG. 7 is a plan view illustrating the operation of the contact lens assembly of an ophthalmic treatment apparatus in accordance with a fourth embodiment of the present invention.

As illustrated in FIG. 7, the ophthalmic treatment apparatus 1 in accordance with the fourth embodiment of the present invention includes the beam generation unit 10, the beam delivery unit 30, and a contact lens assembly 350.

The contact lens assembly 350 of the ophthalmic treatment apparatus 1 in accordance with the fourth embodiment of the present invention includes a housing 352 and a reflection unit 354. In this case, the reflection unit 354 moves along the inner circumferential surface of the housing 352 and guides a beam for treatment incident on the inside of the housing 352 to a plurality of radiation locations. The reflection unit 354 includes a mirror unit 354a and a driving unit 354b.

The mirror unit 354a is disposed within the housing 352 and provided in a sheet form so that it reflects a beam for treatment that is incident on the inside of the housing 352 in the outer circumferential direction of the eyeball O. The driving unit 354b provides a driving force that moves the mirror unit 354a along the inner circumferential surface of the housing 352 so that the mirror unit 354a reflects a beam for treatment in the outer circumferential direction of the eyeball O. As described above, the mirror unit 354a can move along the inner circumferential surface of the housing 352 by a driving force provided by the driving unit 354b and radiate a beam for treatment that is incident on the inside of the housing 352 to a plurality of radiation locations.

An operational process of the ophthalmic treatment apparatus 1 having such a configuration in accordance with the embodiments of the present invention is described below.

The operational process of the ophthalmic treatment apparatus 1 to be described below is described based on the first embodiment, that is, a representative example.

First, the contact lens assembly 50 is brought in contact with the cornea Co of the eyeball O of a patient. Furthermore, the beam generation unit 10 operates and generates a beam for treatment. The beam for treatment generated by the beam generation unit 10 is guided to the contact lens assembly 50 by the beam delivery unit 30.

In this case, the beam for treatment that is incident on the housing 52 of the contact lens assembly 50 is reflected by the reflection unit 54 and radiated to a radiation location according to the circumference of the eyeball O outside the eyeball O. In this case, if the mirror unit 54a of the reflection unit 54 disposed within the housing 52 is configured to rotate or move (the first embodiment and the fourth embodiment), the driving unit 54b provides a driving force to drive the mirror unit 54a so that the incident beam for treatment is radiated to a plurality of radiation locations.

In this case, in the first embodiment, the driving unit 54b of the mirror unit 54a that belongs to the plurality of mirror units and that corresponds to the direction in which the beam for treatment is incident may be controlled based on the operation contents of the beam delivery unit so that the driving unit 54b is driven. In this case, the driving unit 54b may control the rotational operation of the mirror unit 54a based on the operation cycle of the aforementioned shutter so that the rotational operation corresponds to the cycle in which the beam for treatment is radiated.

Meanwhile, in the fourth embodiment, the driving unit 54b may control the mirror unit 54a based on the operation contents of the beam delivery unit and the operation cycle of the shutter by taking into consideration the direction in which the beam for treatment is incident and the cycle in which the beam for treatment is incident so that the location of the mirror unit 54a is moved.

As described above, the reflection unit for illuminating a plurality of radiation locations is disposed in the outer circumferential direction of an eyeball. Accordingly, a beam for treatment can be radiated to a plurality of radiation locations in a short time, and thus treatment efficiency can be improved.

As described above, although the embodiments of the present invention have been described with reference to the accompanying drawings, those skilled in the art to which the present invention pertains will understand that the present invention may be implemented in other detailed forms without changing the technical spirit or indispensable characteristics of the present invention. Accordingly, it will be understood that the aforementioned embodiments are illustrative and not limitative from all aspects. The scope of the present invention is defined by the appended claims rather than the detailed description, and the present invention should be construed as covering all modifications or variations derived from the meaning and scope of the appended claims and their equivalents.

What is claimed is:

1. A contact lens assembly for treating glaucoma, comprising:
   a housing which is configured to be disposed on a cornea of an eyeball; and
   a plurality of reflection units which are disposed within the housing and which guide a beam for treatment that has entered the housing to a plurality of radiation locations, each of the plurality of reflection units comprising a reflector and a drive unit, the drive unit being configured to rotate the reflector, the plurality of radiation locations being arranged in an outer circumferential direction of the eyeball around a pupil of the eyeball and being located proximate to a ciliary body of the eyeball, the beam for treatment being radiated to the plurality of radiation locations in an inclined direction to a central axis of the housing,
   wherein each of the plurality of reflection units has its own rotation axis and is installed rotatably about the rotation axis, the rotation axis being different from the central axis of the housing, the rotation axis intersecting with a plane perpendicular to an optical axis of the eyeball, and
   wherein the plurality of reflection units guide the beam for treatment to the plurality of radiation locations by rotating, the plurality of radiation locations being located on the plane perpendicular to the optical axis.

2. The contact lens assembly of claim 1, wherein each of the reflection units radiates the beam for treatment to at least two locations among the plurality of radiation locations by rotating about the rotation axis, the plurality of radiation locations being arranged in the outer circumferential direction of the eyeball at equal intervals.

3. The contact lens assembly of claim 2, wherein the plurality of reflection units are disposed at equal intervals within the housing, a number of the plurality of reflection units being determined according to a number of the plurality of radiation locations.

4. The contact lens assembly of claim 1, wherein each of the reflection units is provided in a sheet form, and
   the plurality of the reflection units are disposed along an inner circumferential surface of the housing to move a location where the beam for treatment is radiated in the outer circumferential direction of the eyeball.

5. The contact lens assembly of claim 1, wherein the plurality of reflection units are disposed on an inner circumferential surface of the housing.

6. The contact lens assembly of claim 1, wherein the rotation axes of the plurality of reflection units are oblique to the central axis of the housing.

7. The contact lens assembly of claim 1, wherein the rotation axes of the plurality of reflection units are nonparallel to the central axis of the housing.

8. An ophthalmic treatment system for treating glaucoma, comprising:
   a beam generation unit which generates a beam for treatment;
   a beam delivery unit which guides the beam for treatment generated by the beam generation unit to an eyeball; and
   a contact lens assembly which is disposed between the eyeball and the beam delivery unit, the contact lens assembly comprising:
      a housing which is configured to be disposed on a cornea of an eyeball; and
      a plurality of reflection units which are disposed within the housing and which guide a beam for treatment that has entered the housing to a plurality of radiation locations, each of the plurality of reflection units comprising a reflector and a drive unit, the drive unit being configured to rotate the reflector, the plurality of radiation locations being arranged in an outer circumferential direction of the eyeball around a pupil of the eyeball and being located proximate to a ciliary body of the eyeball, the beam for treatment being radiated to the plurality of radiation locations in an inclined direction to a central axis of the housing,
   wherein each of the plurality of reflection units has its own rotation axis and is installed rotatably about the rotation axis, the rotation axis being different from the central axis of the housing, the rotation axis intersecting with a plane perpendicular to an optical axis of the eyeball, and
   wherein the plurality of reflection units guide the beam for treatment to the plurality of radiation locations by rotating, the plurality of radiation locations being located on the plane perpendicular to the optical axis.

9. The ophthalmic treatment system of claim 8, wherein the beam delivery unit controls a radiation path of the beam for treatment that is incident from the beam generation unit and that is radiated to the contact lens assembly.

* * * * *